(12) United States Patent
Drevik et al.

(10) Patent No.: US 8,900,210 B2
(45) Date of Patent: Dec. 2, 2014

(54) ABSORBENT ARTICLE WITH DISPOSAL WRAPPER

(75) Inventors: Solgun Drevik, Mölnlycke (SE); Dennis Dahl, Mölnlycke (SE); Fredrik Karlsson, Landvetter (SE)

(73) Assignee: SCA Hygiene Products AB, Gothenburg (SE)

( * ) Notice: Subject to any disclaimer, the term of this patent is extended or adjusted under 35 U.S.C. 154(b) by 210 days.

(21) Appl. No.: 13/140,216

(22) PCT Filed: Dec. 17, 2008

(86) PCT No.: PCT/SE2008/051482
§ 371 (c)(1),
(2), (4) Date: Aug. 26, 2011

(87) PCT Pub. No.: WO2010/071512
PCT Pub. Date: Jun. 24, 2010

(65) Prior Publication Data
US 2011/0306945 A1    Dec. 15, 2011

(51) Int. Cl.
*A61F 13/551*    (2006.01)
(52) U.S. Cl.
CPC .................... *A61F 13/5515* (2013.01)
USPC ............. 604/385.13; 604/385.02; 604/385.05
(58) Field of Classification Search
CPC ............ A61F 13/5515; A61F 13/5517; A61F 13/5518
USPC .................. 604/354, 385.02, 385.05, 385.11, 604/385.13, 385.19; 383/7; 206/438–441, 206/494
See application file for complete search history.

(56) References Cited

U.S. PATENT DOCUMENTS

| | | |
|---|---|---|
| 3,186,626 A | 6/1965 | Shvetz |
| 4,380,450 A | 4/1983 | Reich |
| 4,548,603 A | 10/1985 | Ichijo |
| 4,556,146 A | 12/1985 | Swanson et al. |
| 4,581,027 A | 4/1986 | Alvarado |
| 4,692,162 A | 9/1987 | Binker et al. |
| 5,358,499 A | 10/1994 | Seidy |
| 5,484,636 A | 1/1996 | Berg, Jr. et al. |
| 5,954,201 A | 9/1999 | Finch et al. |
| 6,520,944 B1 | 2/2003 | Jonbrink |

(Continued)

FOREIGN PATENT DOCUMENTS

| | | |
|---|---|---|
| DE | 196 54 456 | 7/1998 |
| EP | 0 965 317 | 12/1999 |

(Continued)

OTHER PUBLICATIONS

Supplementary European Search Report dated Apr. 3, 2012 in Appln. No. 08878983.9.

*Primary Examiner* — Tan-Uyen T Ho
*Assistant Examiner* — Peter S Vasat
(74) *Attorney, Agent, or Firm* — Drinker Biddle & Reath LLP

(57) ABSTRACT

A kit including an absorbent article and a wrapper for the absorbent article. The wrapper is defined by a boundary. The wrapper includes at least one slit which partitions the wrapper to define a strip thereof. The strip is arranged such that the absorbent article may be rolled and/or folded within the wrapper and retained in a rolled and/or folded configuration by using the strip. Also, a method for disposal of an absorbent article.

10 Claims, 8 Drawing Sheets

(56) References Cited

U.S. PATENT DOCUMENTS

| | | |
|---|---|---|
| 7,413,079 B2 | 8/2008 | Hermansson et al. |
| 2003/0115834 A1 | 6/2003 | Kelley |
| 2005/0069227 A1* | 3/2005 | Steele ................................ 383/7 |
| 2005/0131371 A1* | 6/2005 | Fell et al. ................... 604/385.02 |
| 2007/0149942 A1 | 6/2007 | Arco et al. |
| 2007/0156109 A1 | 7/2007 | Loyd et al. |
| 2008/0058749 A1 | 3/2008 | Tackett et al. |

FOREIGN PATENT DOCUMENTS

| | | |
|---|---|---|
| EP | 0 732 094 | 8/2001 |
| EP | 1 147 756 A2 | 10/2001 |
| EP | 1 035 818 | 4/2002 |
| EP | 1 205 170 | 5/2002 |
| EP | 1 661 537 A1 | 5/2006 |
| GB | 2 386 108 | 9/2003 |
| JP | 11104167 A | 4/1999 |
| RU | 2261078 C2 | 9/2005 |
| RU | 2322959 C2 | 4/2008 |
| WO | 97/16146 | 5/1997 |
| WO | 99/52483 | 10/1999 |
| WO | 99/52485 | 10/1999 |
| WO | 2006/054925 | 5/2006 |

* cited by examiner

ABSORBENT ARTICLE WITH DISPOSAL WRAPPER

CROSS-REFERENCE TO PRIOR APPLICATION

This application is a §371 National Stage Application of PCT International Application No. PCT/SE2008/051482 filed Dec. 17, 2008.

FIELD-OF THE INVENTION

The present disclosure provides an absorbent article which can be secured in a folded configuration for safe, hygienic disposal, as well as a method for hygienic disposal of a soiled absorbent article. At least one slit is provided in a wrapper for the absorbent article, which partitions said wrapper to define at least one strip thereof. The absorbent article can be retained in the rolled up or folded configuration for disposal by means of said at least one strip.

BACKGROUND

Absorbent articles such as diapers, incontinence guards, sanitary napkins and panty liners are used for the absorption of bodily exudates, such as blood, urine, sweat and feces. Absorbent articles are sometimes packaged individually in wrappers, so that the product remains clean and intact prior to use.

After an absorbent article has been used and soiled, a user or caregiver is faced with the problem of safe, hygienic disposal of the absorbent article and its contents. For absorbent articles which are provided with wrappers, such as sanitary napkins, it is common for disposal purposes to roll or fold a used article within the wrapper of the new (unused) article. This technique tends to keep the exudate within the article, and is more aesthetically pleasing, as exudate such as blood is not visible from the outside of the article.

However, without specific means to prevent unrolling or unfolding, folded or rolled absorbent articles are free to open up again, thus soiling waste receptacles and allowing the exudate to be released into the surrounding environment. Indeed, as bodily exudate is slowly redistributed within an absorbent article after use, it is common that a redistribution of the forces within an absorbent article cause it to unfold or unroll.

A number of solutions are known in the art for retaining absorbent articles in a rolled or folded configuration for disposal. Certain absorbent articles can be maintained in a rolled or folded configuration for disposal using existing fastening means on the article. For example, a sanitary napkin having wings including adhesive can be maintained in a folded configuration by adhering the wings to each other or to the body of the napkin (see e.g. U.S. Pat. No. 5,358,499). However, particularly in small sanitary napkins and panty liners, adhesive wings are not always present. In addition, sanitary napkins which have been fastened in a rolled or folded configuration via their wings tend to only be adhered temporarily, and will tend to open again after a short period in a waste receptacle.

A disposal tab (of adhesive or hook material) may be present on the absorbent article. After the absorbent article has been folded up, the disposal tab is deployed to fix the absorbent article in the folded configuration. Such a solution is illustrated in U.S. Pat. No. 4,380,450, and similarly, U.S. Pat. No. 5,484,636. However, the inclusion of a disposal tab involves extra materials and manufacturing costs, and introduces the risk that the disposal tab may fall off or become attached to the wearer's clothing during use.

Another method for securing a soiled absorbent article in a rolled or folded configuration is by providing a pocket on the article into which the folded absorbent article is inserted (e.g. WO 2006/054925). However, this solution requires the formation of the pocket from extra materials. US 2003/0115834 also discloses a pocket in a wrapper.

U.S. Pat. No. 4,692,162 describes a sanitary napkin with an integral disposal wrapper. U.S. Pat. No. 4,581,027 describes a sanitary napkin with an integral disposal bag. US2008/0058749 discloses a tampon wrapper being a polyethylene film tube, in which disposal of a tampon can take place. U.S. Pat. No. 5,954,201, WO 99/52485 and WO 99/52483 disclose individually packaged absorbent articles.

There remains a need for an absorbent article with associated wrapper which can be maintained in a rolled or folded configuration for disposal, in a simple, effective manner, without the requirement for extra components, and with minimal changes to the manufacturing process. In addition, there is a need for an absorbent article with associated wrapper which can be "locked" in a rolled or folded configuration for disposal.

SUMMARY

A kit is provided that includes: an absorbent article; and a wrapper for said absorbent article. The wrapper is defined by a boundary. The wrapper includes at least one slit which partitions said wrapper to define at least one strip thereof. At least one end of each slit does not extend to the boundary of the wrapper, such that each strip remains joined to the wrapper. At least one strip is arranged such that the absorbent article may be rolled and/or folded within the wrapper and retained in a rolled and/or folded configuration by means of said at least one strip. Suitably, the wrapper includes one slit which defines one strip thereof.

In one embodiment, neither end of the slit extend to the boundary of the wrapper, such that the strip forms a loop and said absorbent article is retained in a rolled and/or folded configuration by pulling said at least one loop over at least a portion of the rolled and/or folded absorbent article.

Suitably, the slit is located substantially adjacent one transverse edge of the wrapper. In a particular embodiment, at least one of the ends of the slit is reinforced.

In one embodiment, the slit includes perforations which hold the slit substantially closed when the absorbent article is packaged, but which may be broken to open the slit.

In the kit, the absorbent article may be packaged within said wrapper.

Also, there is provided a method for disposal of an absorbent article after use, said method including the steps of:
 a. providing a kit according to the above;
 b. if required, breaking perforations to open the slit;
 c. rolling and/or folding the used absorbent article within the wrapper; and
 d. retaining the absorbent article in a rolled and/or folded configuration by means of said strip.

DEFINITIONS

The term "absorbent article" is to be understood as meaning an article selected from the group consisting of diapers, male or female incontinence guards, sanitary napkins or panty liners (including articles for use with "string" underwear). Such articles are used for the absorption of bodily exudates, such as blood, urine, sweat and feces.

BRIEF DESCRIPTION OF THE DRAWINGS

Embodiments of the invention will now be described in more detail with reference to the enclosed schematic Figures, in which.

DETAILED DESCRIPTION OF PREFERRED EMBODIMENTS

The present disclosure relates to absorbent articles, but is illustrated in the enclosed figures and the following description with reference to a sanitary napkin.

Absorbent articles have a generally elongate form, and are designed to be worn in the genital region of a wearer, between the wearer's skin and the wearer's clothes to absorb bodily fluids. They generally have two faces—one of which faces the body of the wearer and acts to receive exudate, and the other of which faces the wearer's clothes. The bodily exudate in a used absorbent article is therefore present on one face of such products, and is therefore exposed to the environment and particularly susceptible to leakage.

Figure 1:
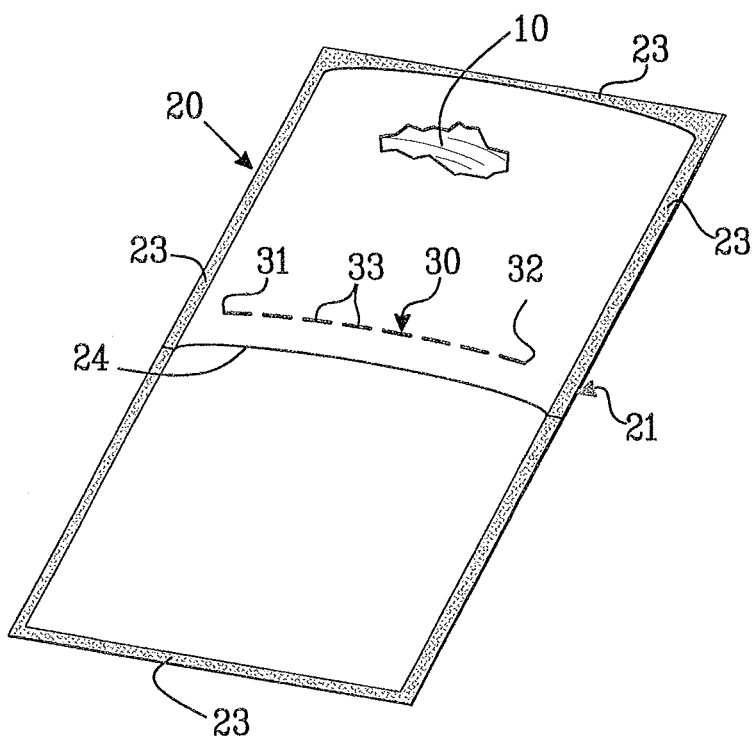
FIG. 1 shows a sanitary napkin packaged in the wrapper of an embodiment of the invention.

FIG. 1 illustrates an absorbent article (in this case a sanitary napkin 10) enclosed in a wrapper 20, as it would be when stored prior to use. In its simplest embodiment, the kit includes an absorbent article 10, and a wrapper 20 for said absorbent article 10.

An absorbent article typically has longitudinal (L) and transverse (T) extensions as shown, and is symmetric about a longitudinal center line. They may also be symmetric about a transverse center line, although this is less common. Sanitary napkins 10 have a variety of shapes in the L-T plane, including oval, "dog-bone", "race-track" "trapezoid" and "mermaid". Absorbent articles 10 are usually planar, which allows for easier transport and packaging, but may even have a three-dimensional form, provided e.g. by extra components or elastics in certain regions. In addition, absorbent articles 10 may include grooves or compression lines which assist liquid flow and spreading, and promote the formation of a three-dimensional form. The illustrated sanitary napkin 10 has a central region 13 and front 11 and rear 12 regions, said central region 13 being located between said front 11 and rear 12 regions in the longitudinal direction. A typical sanitary napkin may have an extension in the longitudinal direction L of between 200 and 300 mm, and an extension in the transverse direction T of between 50 and 90 mm.

Figure 2:
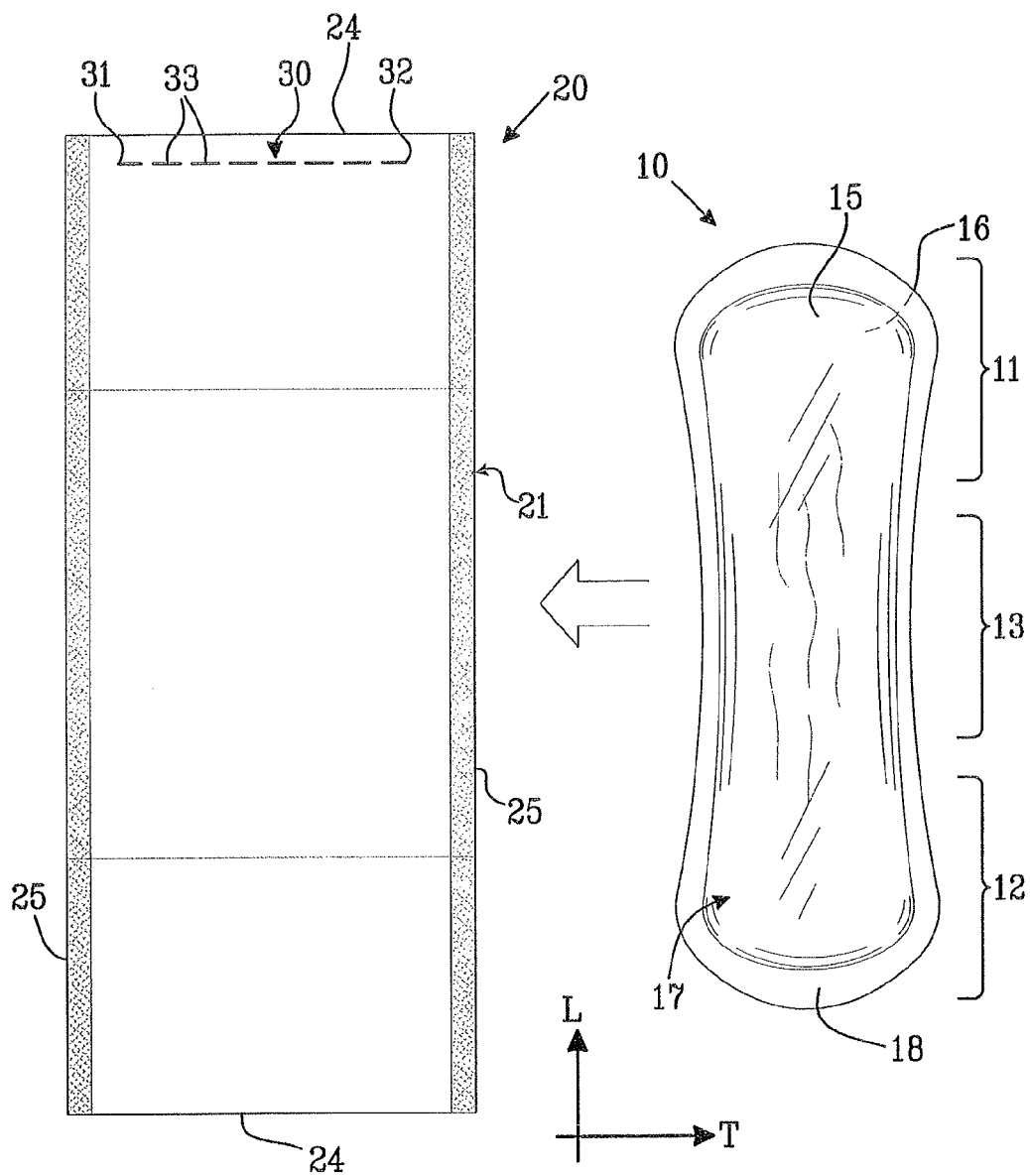
FIG. 2 shows a plan view of a sanitary napkin and wrapper of FIG. 1, prior to use seen from the wearer-facing side.

The absorbent article 10 shown in FIG. 2 includes a liquid-permeable topsheet 15, a liquid-impermeable backsheet 16 and an absorbent core 17 located therebetween. However, not all absorbent articles include all of these components. Certain small panty liners do not include an absorbent core 17 as such, but instead include additional layers of material, e.g. nonwoven material, in the certain regions thereof. Additionally, certain absorbent articles do not include separate topsheets 15 or backsheets 16.

The topsheet 15 of the absorbent article 10 is the layer which lies in contact with the wearer's body when the article is in use. As such, it should be soft, non-irritating and comfortable against the skin, and bodily fluid should be able to pass through it without hindrance. The topsheet 15 can include a nonwoven material, e.g. spunbond, meltblown, carded, hydroentangled, wetlaid etc. Suitable nonwoven materials can be composed of natural fibers, such as woodpulp or cotton fibers, manmade fibers, such as polyester, polyethylene, polypropylene, viscose etc. or from a mixture of natural and manmade fibers. The topsheet may further be composed of tow fibers, which may be bonded to each other in a bonding pattern, as e.g. disclosed in EP-A-1 035 818. Further examples of materials suitable for topsheets are porous foams, apertured plastic films etc. The topsheet 15 may be different in different parts of the absorbent article 10.

The backsheet 16 of the absorbent article 10 is the layer which lies furthest from the wearer's body when the article is in use. To protect the wearer's garments from soiling, it should be liquid-impermeable, but is desirably gas-permeable (i.e. breathable) to allow air and vapor to pass in and out of the article so that the warm, damp conditions which can arise in a diaper are reduced. Typically, the backsheet 16 is of a liquid impervious material, such as a thin plastic film, e.g. a polyethylene or polypropylene film, a nonwoven material coated with a liquid impervious material, a hydrophobic nonwoven material, which resists liquid penetration or a laminate including plastic films and nonwoven materials. Examples of breathable backsheet materials are porous polymeric films, nonwoven laminates from spunbond and meltblown layers, laminates from porous polymeric films and nonwovens. The backsheet 16 may be different in different parts of the absorbent article 10.

The absorbent core 17 of the absorbent article 10 acts to receive and contain liquid and other bodily exudates and can be of any conventional kind. As such, it typically includes absorbent material. Examples of commonly-occurring absorbent materials are cellulosic fluff pulp, tissue layers, highly-absorbent polymers (so called superabsorbents), absorbent foam materials, absorbent nonwoven materials or the like. It is common to combine cellulosic fluff pulp with superabsorbents in an absorbent body. It is also common to have absorbent cores including layers of different material with different properties with respect to liquid receiving capacity, liquid distribution capacity and storage capacity. The thin absorbent cores, which are common in, for example baby diapers and incontinence guards, often include a compressed mixed or layered structure of cellulosic fluff pulp and superabsorbent. The size and absorbent capacity of the absorbent core 17 may be varied to be suited for different uses such as for infants or for incontinent adults.

The absorbent core 17 may include one or more layers which are designed to improve the handling of bodily waste. Such layers are designed to receive a large amount of liquid in a short space of time and distribute it. They may include so-called transfer, distribution, surge or acquisition layers, and are usually located between the topsheet 15 and the absorbent core 17.

The topsheet 15 and backsheet 16 generally have a similar extension in the plane of the article, while the absorbent core 17 has an extension which is somewhat smaller. The topsheet 15 and backsheet 16 are joined to one another around the periphery of the absorbent core 17, so that the core 17 is enclosed within the envelope formed by the topsheet 15 and the backsheet 16. The absorbent core 17 is at least located in the central region 13 of the absorbent article 10, and may also extend somewhat into the front 11 and rear 12 regions. The topsheet 15 and backsheet 16 may be joined to one another by any means common in the art, e.g. ultrasonic welding, thermal welding or gluing.

The wrapper 20 is arranged about the absorbent article 10 prior to use, and protects it from the environment. The wrapper 20 therefore has dimensions such that it can cover the absorbent article 10 substantially entirely prior to use. However, the wrapper 20 may also take the form of a ribbon, which does not cover the entire absorbent article 10. When packaged within the wrapper 20 prior to use, the absorbent article 10 is usually folded one or more times, typically twice, so the dimensions of the wrapper depend somewhat on the configuration of the absorbent article 10 when packaged. The wrapper 20 is defined by a boundary 21.

Absorbent articles which are individually wrapped are usually wrapped in one of two ways. A "single wrap" includes a wrapper which is folded and sealed to form an envelope. The article is folded, inserted into the envelope, and the wrapper envelope is sealed. A single wrap is illustrated in FIG. 1. Further details of a "single wrap" may be obtained from U.S. Pat. No. 7,413,079. A "quick wrap" is an alternative form of wrapping absorbent articles, in which the article and wrapper are placed together, and then article and wrapper are folded together, so that a portion of the wrapper usually lies interfolded with the article.

In the packaged state, the wrapper 20 is sealed about the edges of the absorbent article 10 at seal 23. Sealing methods include ultrasound, adhesive, laser, crimping, cold rolling, mechanical or thermal sealing, and the best method is selected depending on the material of the wrapper 20 and the strength at which the wrapper 20 is to be bonded. It should be possible to remove the wrapper 20 from the absorbent article 10 by breaking the edge seal. Suitably, the wrapper 10 is arranged such that a fold or edge of the wrapper 20 is located on one face of the absorbent article 10, allowing for easy opening of the wrapper 20. The wrapper 20 is suitably not integral with the absorbent article 10; i.e. it includes a separate piece of material which does not remain attached to the absorbent article 10 when the article is in use.

Typically, the wrapper 20 includes a substantially rectangular or square piece of material, the longitudinal (L) and transverse (T) extensions of which are slightly greater (e.g. 1-4 cm greater at each edge) than those of the absorbent article 10 (see e.g. FIG. 2). The wrapper 20 is defined by a boundary 21. Prior to use in disposal of the absorbent article 10, the wrapper 20 is suitably substantially planar (i.e. exists in one plane without pockets, folds or seams).

The wrapper 20 may include a range of suitable materials. In particular embodiments, the material of the wrapper 20 should be liquid-impervious, recyclable and/or biodegradable. Suitable materials include plastic films, nonwoven webs and laminates thereof. Plastic films are preferred, as are laminates of plastic films and nonwoven materials. The wrapper may be reinforced, with additional materials located in various regions thereof. The wrapper 20 may include the release paper of the absorbent article 10 (the release paper is the paper which covers any adhesive present on the backsheet, prior to use). As such, the wrapper 20 functions as both release paper and packaging. As such, the wrapper 20 may be coated with a layer of e.g. silicone or similar agent which provides the wrapper with release properties. Alternatively, the wrapper 20 may be separate from the release paper. The material of the wrapper 20 is suitably extensible (i.e. it can be stretched without significant elastic forces being present which return it to its original dimensions).

Figure 6A:
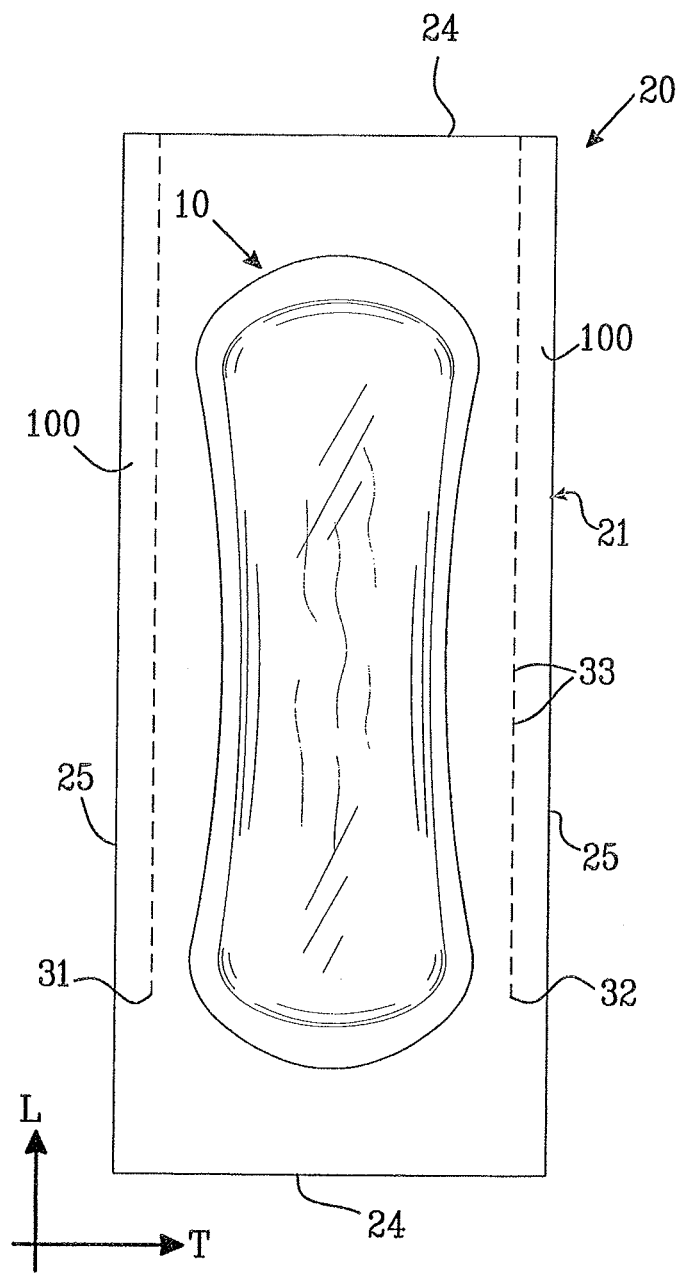
FIGS. 6A and 6B show an alternative embodiment, in which two slits are present, each of which extends to one edge of the wrapper.

The wrapper 20 includes at least one slit 30, as seen in FIGS. 1, 2 and 6A. The slit 30 partitions the wrapper 20 to define at least one strip 100 thereof. At least one end 31, 32 of each slit 30 does not extend to the boundary 21 of the wrapper 20, so that each strip remains joined to the wrapper 20 throughout the use of the wrapper 20.

In the embodiment of FIGS. 1 and 2, neither end of the slit 30 extends to the boundary 21 of the wrapper 20. In this way, a strip 100 is created which has the form of a loop 45. In the embodiments of FIGS. 6A, 6B, 7A and 7B, one end of each of two slits 30 extends to the boundary 21 of the wrapper 20, and two strips 100 are thus created which are joined to the remainder of the wrapper at one end thereof.

In whichever embodiment, the slit 30 extends completely through the entire wrapper 20, from one face to the other. The slit 30 suitably can take the form of a single line, e.g. a straight line, but it may also be curved or angled so as to follow the edges and/or contours of the wrapper 20. The slit 30 may also take the form of one or more adjoining lines. For example, the slit 30 may be formed of a single line, which is joined to one or more shorter lines (e.g. in a T-shape, or a Y-shape), or a sinusoidal (S-shaped) line. In this way, the slit 30 can open to a greater extent than if it had been a single line.

In particular embodiments, only one slit 30 is present in the wrapper 20, which defines one strip 100. However, two slits 30 may be present, as, for example, per FIGS. 6-7. The slit 30 may be located adjacent one transverse edge 24, or one longitudinal edge 25 of the wrapper 20, and suitably parallel therewith. The slit 30 may also be located on a corner of the wrapper 20, i.e. the slit 30 is located adjacent both a transverse edge 24 and a longitudinal edge 25 of the wrapper 20. Placing the slit 30 on the corner of the wrapper 20 allows the slit 30 to open further than it would if it were only placed adjacent one edge.

In particular embodiments, the slit 30 is located within 2.5 cm from an edge of the wrapper 20, more preferably within 1.5 cm, most preferably within 1 cm. However, placing the slit 30 too close to the edge of the wrapper 20 makes the strip 100 too thin, and the risk of breakage arises. Therefore, in particular embodiments, the slit 40 is located at least 0.3 cm, more preferably at least 0.5 cm from the edge of the wrapper 20.

The slit 30 suitably has a length of between 20 and 100 mm, preferably between 30 and 80 mm, more preferably circa 50 mm. If the slit 30 is branched, or includes more than one line, this length should be considered as the longest length of a single line included in said slit 30.

Suitably, at least one of the ends 31, 32 of the slit 30 is reinforced. Reinforcement reduces the risk of the loop 45 breaking and/or the slit 30 tearing beyond the required distance. Reinforcement can be carried out by e.g. addition of adhesive at the ends 31, 32 of the slit 30, addition of extra material at least at the ends 31, 32 of the slit 30, and/or welding and/or melting the material of the wrapper 20 at said ends 31, 32.

Figure 3:
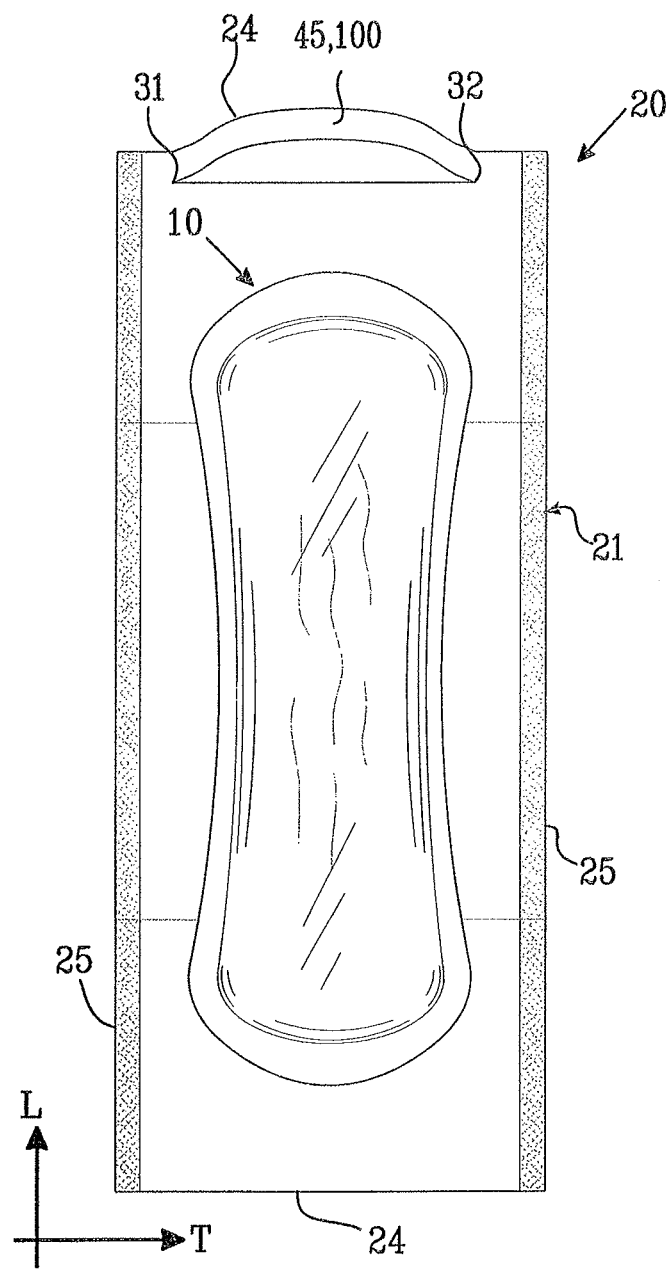
FIG. 3 shows the sanitary napkin and wrapper of FIG. 1 overlaid ready for rolling, with the perforations in the wrapper broken.
Figure 6B:
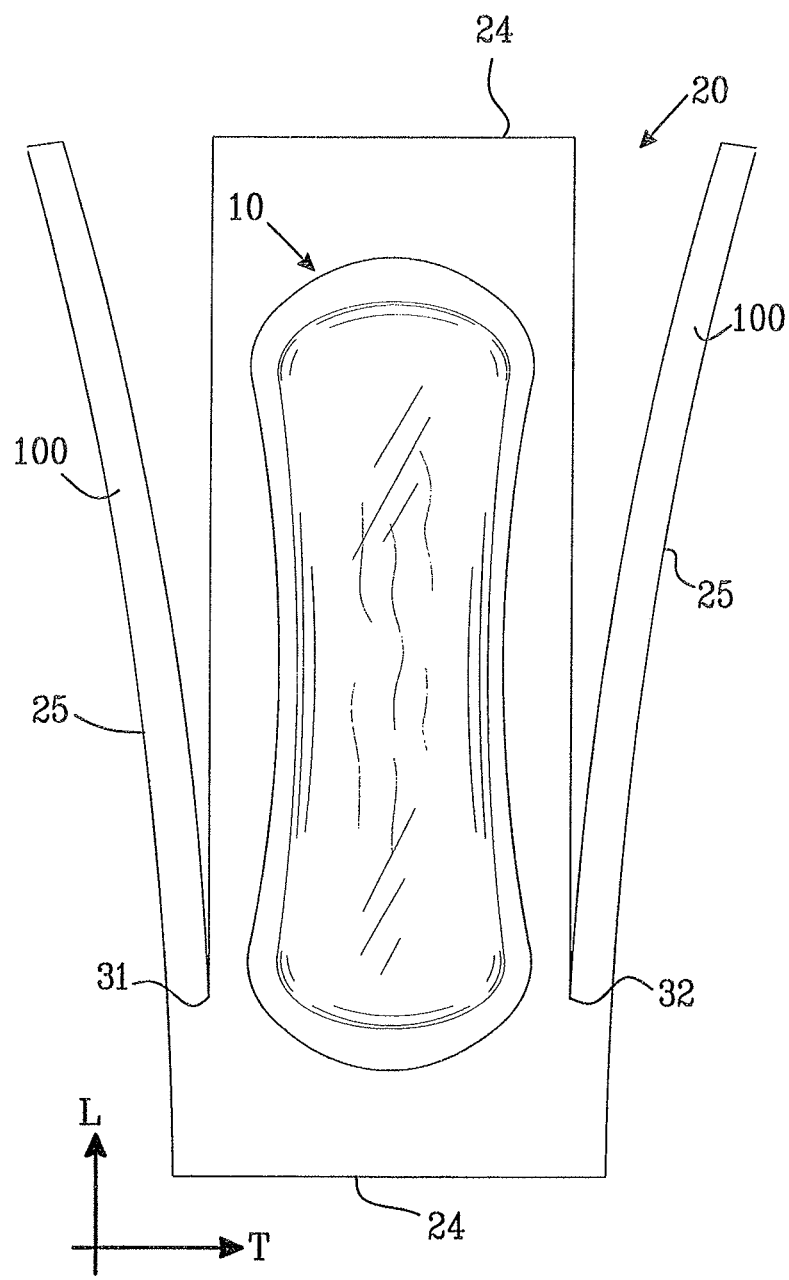

The slit 30 may include perforations 33 so that the slit 30 is held substantially closed when the absorbent article 10 is packaged within the wrapper 10, but which may be broken (i.e. interconnected) to open the slit 30. Perforations 33 are typically spaced at regular intervals along the length of the slit 30 (e.g. 1-15 mm intervals), and have a typical extension in the direction of the slit of between 1 and 15 mm. The provision of perforations 33 provides the wearer with visual reassurance of a "complete" wrapper, and hinders dirt dust and liquids from entering the package of the absorbent article 10. In particular embodiments, the perforations 33 are easier to break towards the middle of the slit 30 than at the ends 31, 32 thereof. This provides a similar effect to reinforcement of the ends, in that opening the slit 30 becomes more difficult closer to the ends 31,32. FIGS. 3 and 6B show how perforations 33 may be broken to form the strips 100.

The slit 30 may also include tear indications, which take the form of printed or embossed indications on the wrapper 20. Tear indications show a user where the slit 30 is located in the wrapper 20, and how the wrapper 20 should be torn to break the perforations 33. Tear indications may include one or more dotted or dashed lines printed on the wrapper 20. Alternatively, the tear indications may take the form of e.g. arrows, color, printed text or icons in the region of the slit 30, which indicate in which direction and where or how a user should pull the wrapper 20 to open the slit 30.

The slit 30 partitions the wrapper 20 so as to define at least one strip 100 thereof. The strip 100 is arranged such that the absorbent article 10 may be rolled and/or folded within the wrapper 20 and retained in a rolled and/or folded configuration by means of said strip 100.

In the embodiment of FIGS. 1-5, the slit 30 does not extend to the boundary 21 of the wrapper 20. The strip 100 therefore takes the form of a closed loop 45, as shown in FIG. 3.

The absorbent article 10 may be rolled and/or folded within the wrapper 20 and at least a portion of the rolled and/or folded absorbent article 10 inserted at least partly through said at least one slit 30 to secure the absorbent article 10 in a rolled and/or folded configuration. Rolling and/or folding for disposal most usually takes place with the topsheet 15 located on the inside of the roll/fold, so that bodily exudate is retained within the absorbent article 10. Most commonly, the absorbent article 10 is rolled within the wrapper 20 rather than folded.

The absorbent core 17 of the absorbent article 10 is more resilient than the fringe 18 thereof. Suitably, therefore, the slit 30 is arranged such that a portion of the absorbent core 17 may be inserted at least partly through the slit 30 to secure the absorbent article 10 in a rolled and/or folded configuration.

When a soiled absorbent article 10 is to be changed for a clean one, the clean absorbent article 10 is removed from its wrapper 20 and placed in position on the wearer. The soiled absorbent article 10 may then be rolled and/or folded within the wrapper 20 in which the clean absorbent article 10 was packaged.

To retain the absorbent article 10 in its rolled and/or folded configuration, the strip 100 in the wrapper 20 is arranged such that said at least one strip 100 may be wrapped and/or tied about the rolled and/or folded absorbent article 10 so as to retain it in a rolled and/or folded configuration. If the strip 100 is in the form of a loop 45, the loop 45 may be pulled over at least a portion of the rolled and/or folded absorbent article 10 (i.e. at least a portion of the rolled and/or folded absorbent article 10 is inserted at least partly through said at least one loop 45).

Figure 4A:
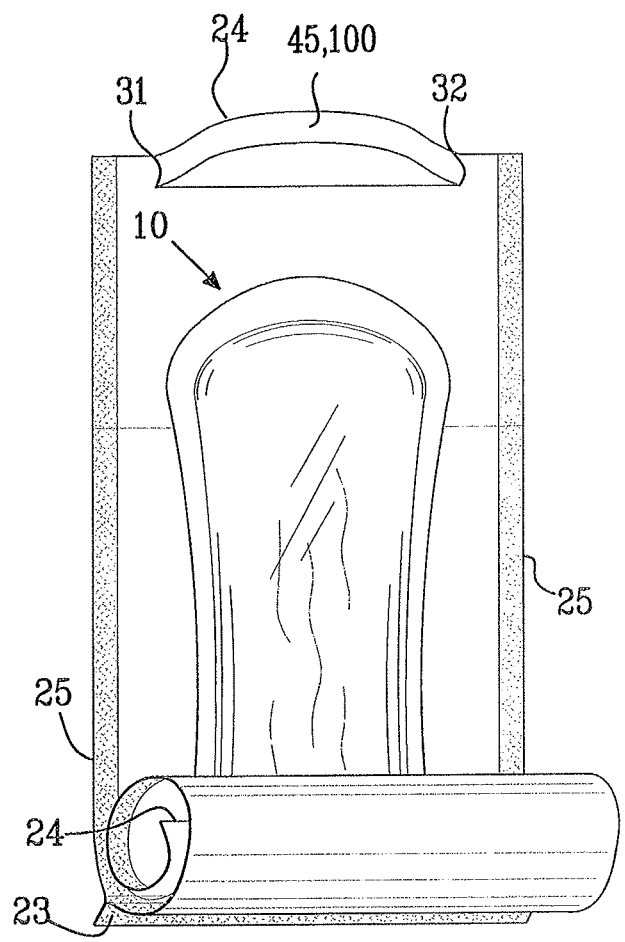
FIG. 4A shows how the sanitary napkin may be rolled within the wrapper of FIG. 1.
Figure 4B:
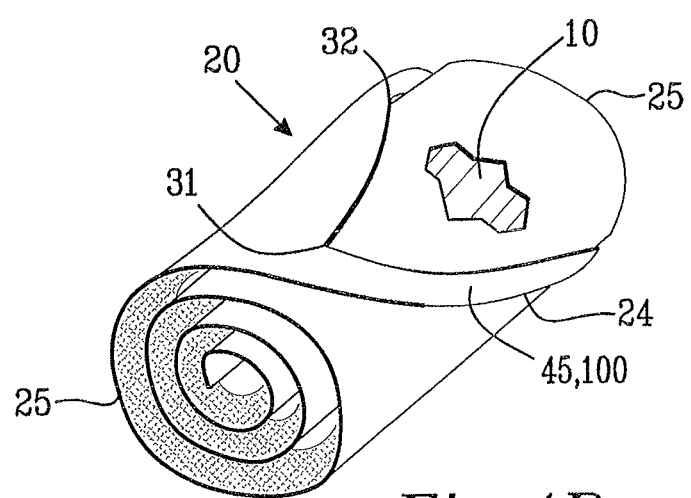
FIG. 4B shows how the rolled sanitary napkin and wrapper of FIG. 4A are retained in the rolled configuration.

This may be carried out as shown in FIGS. 4A and 4B. FIG. 4A shows how the absorbent article 10 to be disposed is placed on the wrapper 20, and the wrapper 20 and absorbent article 10 are rolled together. FIG. 4B shows how the rolled wrapper 20 and absorbent article 10 are retained in the rolled configuration by inserting the roll through the loop 45.

As an alternative to the method illustrated in FIGS. 4A and 4B, the absorbent article 10 may be rolled upon itself first, then placed within the wrapper 20 and the wrapper 20 may then be rolled about the rolled absorbent article 10.

Figure 5A:
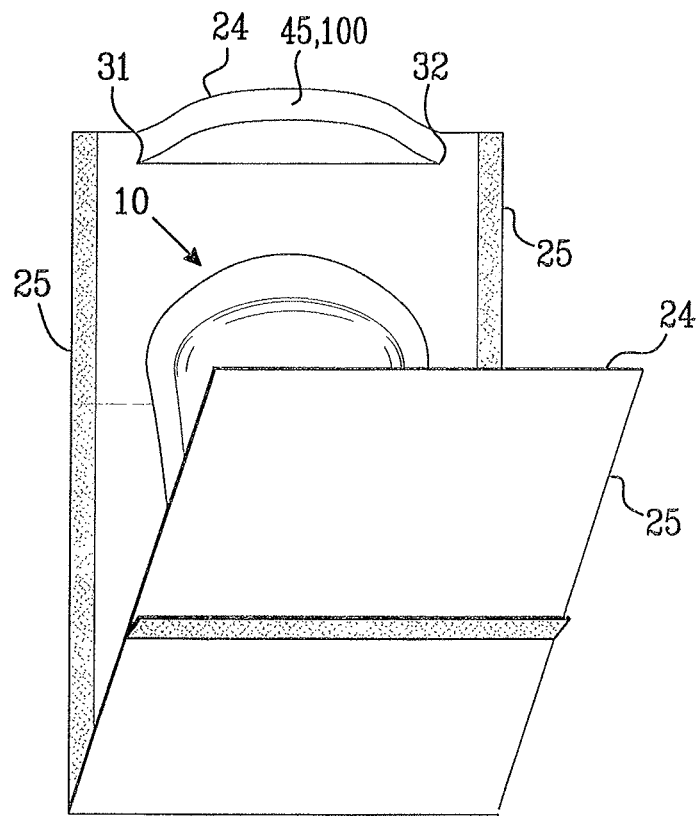
FIG. 5A shows how the sanitary napkin may be folded within the wrapper of FIG. 1.
Figure 5B:
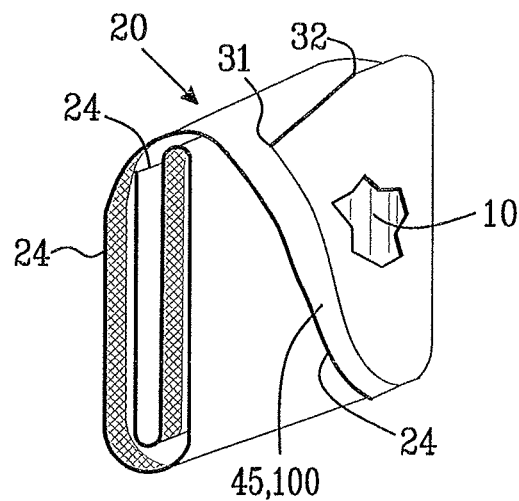
FIG. 5B shows how the rolled sanitary napkin and wrapper of FIG. 5A are retained in the folded configuration.

Alternatively, the absorbent article 10 may be folded as shown in FIGS. 5A and 5B. FIG. 5B shows how the absorbent article 10 to be disposed is placed on the wrapper 20, and the wrapper 20 and napkin 10 are folded together. FIG. 5B shows how the folded wrapper 20 and absorbent article 10 are retained in the folded configuration by inserting one end of the absorbent article 10 through the loop 45.

In addition to the rolled and folded configurations shown in FIGS. 4A, 4B, 5A and 5B, a variety of other rolled and/or folded configurations exist, which can be retained in place by inserting at least a portion of the rolled and/or folded absorbent article 10 through the slit 30. For instance, the absorbent article 10 could be folded within the wrapper 20 along one, three or more fold lines, to form a double-fold or quadruple-fold, instead of the triple-fold shown in FIG. 5. The absorbent article 10 could be folded in two or more different directions, e.g. folded into quarters. A combination of folding and rolling could be used: e.g. by folding the absorbent article 10 in half in one direction, then rolling the folded article 10.

Rolling and folding takes place so that the strip 100 is not incorporated into the folded or rolled absorbent article 10, but rather remains outside the folds/rolls, so that it can be used as described.

FIGS. 6A, 6B and 7A and 7B illustrate an alternative embodiment, in which two slits extend to the boundary 21 of the wrapper 20. At least one strip 100 is thus created which is joined to the remainder of the wrapper at one end thereof. The material of the wrapper 20, and the nature and placement of the slits 30 and the strip 100 in the embodiment of FIG. 1 also applies to this embodiment, apart from the fact that the slits 30 extend to the boundary 21 of the wrapper 20.

Figure 7A:
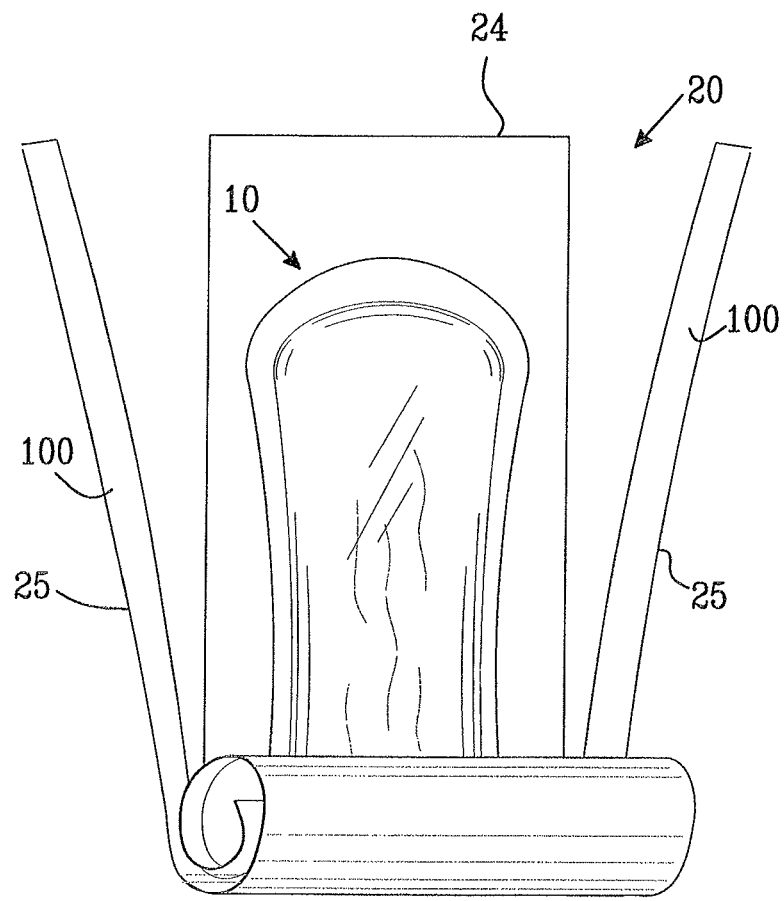
FIGS. 7A and 7B show how the embodiment of FIGS. 6A and 6B is used.
Figure 7B:
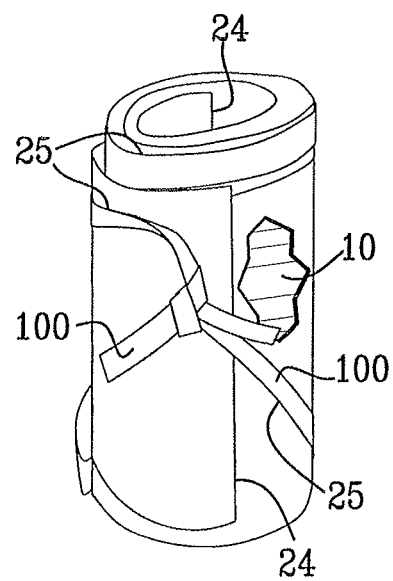

FIGS. 7A and 7B illustrate how the wrapper 20 of FIGS. 6A and 6B might be used. A used absorbent article 10 is placed on the wrapper 20, and rolled such that the soiled article 10 is located inside the wrapper 10. The article 10 is secured in its rolled/folded state by tying or otherwise fastening the two strips 100 around the rolled up article 10.

As above, the example illustrated in FIGS. 7A and 7B are merely illustrative, and many other ways of folding and/or rolling the absorbent article 10 within the wrapper 20 can be imagined, as set out in the first embodiment above. For instance, the wrapper 20 may only include one slit 30, which provides only one strip 100. The absorbent article 10 may be retained in its rolled/folded configuration by wrapping a single strip 100 about the folded/rolled article 10, and securing the strip 100.

The present disclosure also provides a method for disposal of an absorbent article 10 after use, said method including the steps of:
  a. providing a kit 10 according to the above;
  b. if required, breaking perforations 33 to open the slit 30;
  c. rolling and/or folding the used absorbent article 10 within the wrapper 20; and
  d. retaining the absorbent article 10 in a rolled and/or folded configuration by means of said strip 100.

Although the invention has been described with reference to a number of embodiments and Figures, it should not be considered as being limited thereto. In particular, the invention is equally applicable to absorbent articles other than sanitary napkins, such as diapers, incontinence guards and panty liners. Variations of materials, components, elements and their locations will be readily understood by persons skilled in the art. The scope of protection should therefore be defined by the enclosed claims.

The invention claimed is:

1. A kit comprising:
   an absorbent article selected from the group consisting of diapers, male or female incontinence guards, sanitary napkins or panty liners; and
   a wrapper for said absorbent article, said wrapper being defined by a boundary having edges,
   wherein the wrapper comprises at least one slit which partitions said wrapper to define at least one strip thereof, the slit having a longitudinal extension adjacent to only one edge of the boundary,
   wherein neither end of said slit extend to the boundary of the wrapper, such that each strip forms a loop and is arranged such that the absorbent article may be rolled and/or folded together with the wrapper and retained in a rolled and/or folded configuration by pulling said at least one loop over at least a portion of the rolled and/or folded absorbent article, and
   wherein the absorbent article is packaged within said wrapper prior to use.

2. The kit according to claim 1, wherein the wrapper comprises one slit which defines one strip thereof.

3. The kit according to claim 1, wherein the slit is located substantially adjacent one transverse edge of the wrapper.

4. The kit according to claim 1, wherein at least one end of the slit is reinforced.

5. The kit according to claim 1, wherein the slit comprises perforations which hold the slit substantially closed when the absorbent article is packaged, but which may be broken to open the slit.

6. The kit according to claim 1, wherein the absorbent article is packaged within said wrapper prior to use.

7. The kit according to claim 1, wherein the wrapper comprises one slit formed by a straight line.

8. The kit according to claim 1, wherein the slit is formed by a single line joined to one or more shorter lines.

9. The kit according to claim 1, wherein the wrapper comprises one slit formed by a sinusoidal line.

10. A method for disposal of an absorbent article after use, said method comprising the steps of:
    providing a kit according to claim 1;
    if required, breaking perforations to open the slit;
    rolling and/or folding the used absorbent article together with the wrapper; and
    retaining the absorbent article in a rolled and/or folded configuration by pulling said at least one loop over at least a portion of the rolled and/or folded absorbent article.

* * * * *